Figure 1:
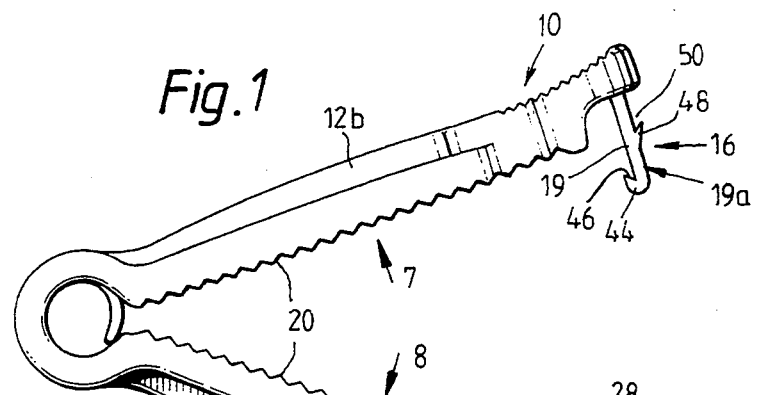

United States Patent [19]

Nates

[11] Patent Number: 5,423,831
[45] Date of Patent: Jun. 13, 1995

[54] CLAMP

[76] Inventor: Colin Nates, 47 Erlswold Road, Saxonwold, Johannesburg, South Africa, 2195

[21] Appl. No.: 139,053

[22] Filed: Oct. 21, 1993

Related U.S. Application Data

[63] Continuation of Ser. No. 819,808, Jan. 13, 1992, abandoned.

[30] Foreign Application Priority Data

Jan. 24, 1991 [ZA] South Africa .................. 91/0542

[51] Int. Cl.[6] .......................................... A61B 17/04
[52] U.S. Cl. ..................... 606/120; 606/157; 24/543; 24/562; 24/598.2
[58] Field of Search ............. 606/120, 157; 24/543, 24/562, 598.2

[56] References Cited

U.S. PATENT DOCUMENTS

| D. 190,787 | 6/1961 | Schneider | 606/120 |
|---|---|---|---|
| 3,247,852 | 4/1966 | Schneider | 606/120 |
| 3,825,012 | 7/1974 | Nicoll | 24/543 |
| 3,854,482 | 12/1974 | Laugherty et al. | 24/543 |
| 4,212,303 | 7/1980 | Nolan | 606/120 |
| 4,870,965 | 10/1989 | Jahanger | 606/120 |
| 5,009,657 | 4/1991 | Cotey et al. | 606/120 |
| 5,050,272 | 9/1991 | Robinson et al. | 24/543 |

FOREIGN PATENT DOCUMENTS 1335672 10/1973 United Kingdom ............ 606/120

*Primary Examiner*—Gary Jackson
*Attorney, Agent, or Firm*—Cushman, Darby & Cushman

[57] ABSTRACT

A plastics umbilical cord clamp is disclosed. This clamp has a pair of arms having their inner ends joined by a hinge and their outer ends connected by a locking device. The device comprises one member having a body with a transverse groove therein and a second member comprising a tongue with hook which engages in the groove. The first mentioned member further comprises a cross-bar spaced away from and above the groove and the tongue is capable of being inserted between the cross-bar and the body. The tongue also has a projection to engage the cross-bar when the hook engages in the groove.

3 Claims, 1 Drawing Sheet

CLAMP

This is a continuation of application No. 07/819,808, filed on Jan. 13, 1992, which was abandoned upon the filing hereof.

This invention relates to clamps and particularly but not exclusively to clamps for medical and/or surgical use and especially for umbilical clamps.

BACKGROUND TO THE INVENTION

It is well known that the umbilical cord of a newly born baby must be closed to prevent bleeding. Previously this was done by knotting the umbilical cord or by means of a tie string. More recently however this closing has been done by means of a clamp and in particular by a clamp made of plastics material.

A typical prior plastics umbilical cord clamp is disclosed in U.S. Pat. No. 3,247,852 to Schneider. This clamp is of the kind comprising a pair of arms having their inner ends joined by a hinge and their outer ends connected by a locking device in the form of a hook portion which is located at one end and which is receivable in a recess in the other end for locking the outer ends together. This cord clamp has a number of disadvantages. First, it lacks visual means for indicating to the user that complete latching or locking has taken place. A second disadvantage is that the hook can be moved, or indeed under certain circumstances may itself move, out of engagement with the recess. Thus the locking or latching is not permanent which is dangerous and potentially fatal.

Another prior plastics umbilical cord clamp of the above kind is disclosed in U.S. Pat. No. 4,212,303 Nolan. This is an extremely popular and widely used umbilical cord clamp. This cord clamp has, instead of a hook, a tongue with a pair of lateral notches which receive projections on the other end member when the clamp is fully closed. In these circumstances the tip of the tongue is received within a recess beneath the projections. This arrangement serves to prevent the tongue being withdrawn from the notches under forces tending to force the two arms apart. However it is possible to manipulate the tongue to cause it to disengage the projections so that the tongue is moved out of engagement with the projections whereby the arms are able to move apart. Thus this cord clamp also does not provide a permanent latching and locking.

SHORT DESCRIPTION OF THE INVENTION

I have found that in order to provide a permanent latching or locking one can provide a double locking arrangement in which any action that tends to open one of the interlocking parts will have the effect of forcing the other pair of interlocking parts more firmly into engagement.

According to one aspect of the invention there is provided a clamp of the kind set forth in which one member has a body with a transverse groove therein and a retaining means located spaced away from and above the said groove and the tongue is capable of being inserted between the retaining means and the body and has a first projection to engage in the groove and a second projection to engage the retaining means when the first projection engages in the groove.

The said groove preferably has its surface closer to the other of the arms formed with a re-entrant angle and the said first projection has a corresponding upper surface to engage said groove surface. The retaining means preferably has a pointed lower surface and the upper surface of the said second projection is correspondingly shaped so as to receive tightly said pointed lower surface. Thus if any force is applied to the arms tending to move said members apart, the said surfaces are forced into closer contact.

The retaining means is preferably in the form of a bar extending across the said body. It is preferably spaced away from the groove so that the part of the tongue with the first member thereon has to pass between the bar and the body in moving to engage the groove. The relative location of the groove and retaining means and the said two members is preferably such that the second member engages the retaining means at the same time as the first member engages the groove.

The facing surfaces of the arms are preferably of interengaging serrated shape and a longitudinal shallow slot may be provided in one or both arms.

An embodiment of the invention will now be described by way of example with reference to the accompanying drawings.

SHORT DESCRIPTION OF THE DRAWINGS

Figure 3:
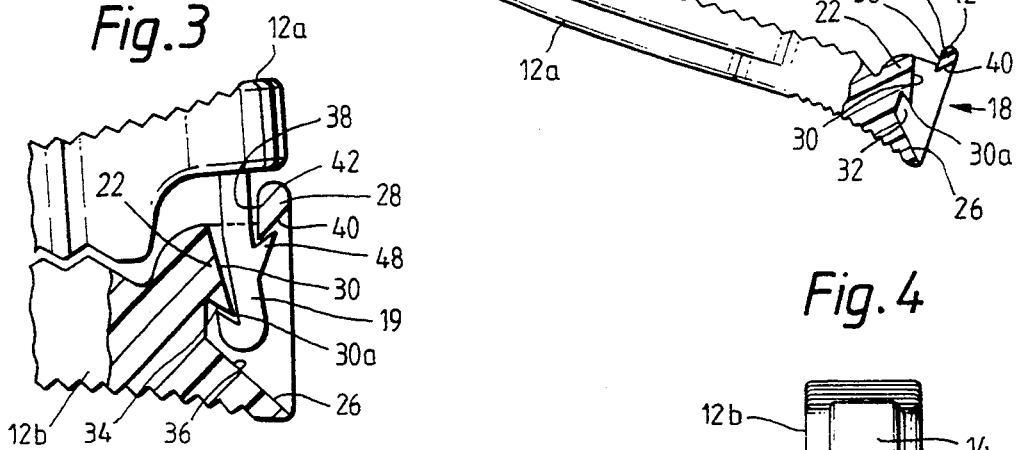
Figure 4:
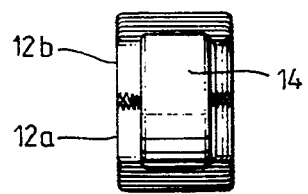
Figure 2:
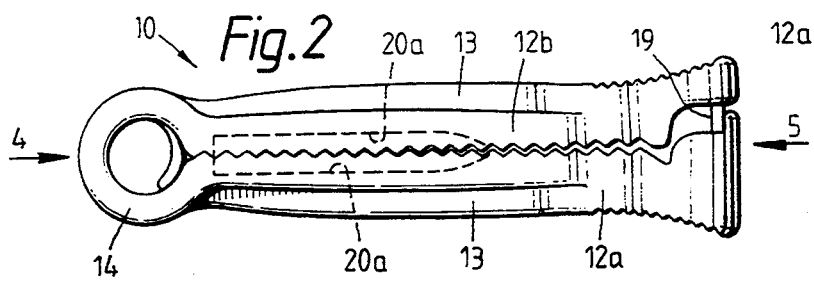
Figure 5:
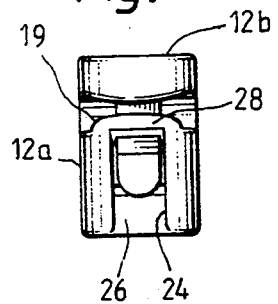
Figure 6:
Figure 7:
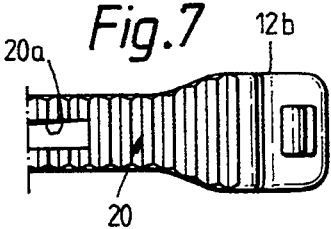
Figure 8:
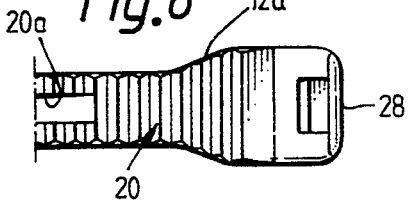

FIG. 1 is a side view, partially in section, of an umbilical clamp of the invention in the open position, FIG. 2 is a side view of the clamp in the closed position, FIG. 3 is an enlarged detail section showing the locking members in the closed position, FIGS. 4 and 5 are respectively end views in the direction of arrows 4 and 5 in FIG. 2, FIG. 6 is a plan of the clamp, and FIGS. 7 and 8 are respectively detail views in the direction of arrows 7—7 and 8—8 of FIG. 1.

Referring now to the drawings, there is shown a clamp 10 for clamping the umbilical cord of a new born baby. The clamp 10 is made of a substantially rigid plastic which is capable of slight flexing such as Nylon. It comprises a pair of arms 12a and 12b joined together at their inner ends by an integral circular hinge 14 and having locking members 16 and 18 at their outer ends. A reinforcing spine 13 runs along the outside surfaces of the arms. The facing surfaces 20 of the arms are of substantially constant width from their join with the hinge 14 and then widen out near the locking members. The surfaces 20 have a serrated interengaging shape. A central shallow longitudinal slot 20a extends in the surface 20 for about two thirds the length of each surface 20 and is about one third of the width of the major part of the surface 20.

The locking member 18 at the end of the arm 12a comprises a body part 22 and two side walls 24 projecting therefrom. A base member 26 joins the lower ends of the side walls 24. A cross-bar 28 extends between the side walls 24 near their upper ends.

The front face 30 of the body part 22 inclines slightly forwardly and there is a slot 32 therein above the base member 26. The upper and lower surfaces 34 and 36 of the slot 32 are inclined and the upper surface of the base member 26 is a continuation of the lower surface 36 of the slot 32. It will be seen that there is a pointed corner 30a at the intersection of the face 30 and the surface 34.

The cross-bar 28 has a forward face 38 and an underface 40 which also meet at a sharp intersection (which arrangement is what is meant by the words "a pointed lower surface" as used herein) and a rounded top surface 42.

The locking member 16 includes a tongue 19 which fits between the side walls 24. At its lower end, it has a rearwardly extending hook or enlargement 44 having an upper surface 46 inclined at about the same angle as the upper surface 34 of the slot.

On the upper part of the forward face of the tongue 19 is a projection 48 having a reentrant opening 50 into which the pointed corner of the cross-bar 28 can be received.

The enlargement 44 and the projection 48 both extend across the entire width of the tongue 19. They are located so that when the upper point of the enlargement 44 passes pointed corner of the slot 32, the upper part of the projection 48 passes the sharp intersection of the cross-bar 28. Thus there will be a simultaneous and positive engagement of the enlargement 44 with the slot 32 and the projection 48 and the cross-bar 28 when the clamp is in the closed position.

On closing the arms 12a and 12b of the clamp together, as the enlargement 44 runs down the face 30 it will be urged to bias the tongue 19 to flex outwardly, which urging is counteracted by the cross-bar 28 acting against the front face 19a of the tongue 19. Thus there will be a sprung interengagement of the parts as mentioned in the preceding paragraph. There will be an audible "snap" so that the person applying the clamp will be able both to see and to hear the engagement of the locking means. It will be appreciated that there is a double locking of the two parts to one another. Once engaged the locking means will be permanently locked together. Any attempt to force the arms 12a and 12b apart will have the effect of causing the locking means 16 and 18 to engage more firmly. Furthermore if a person endeavoured to pull the tongue forwardly so that the hook disengaged from the recess 32, the part 48 would be forced more firmly against the cross-bar 28 preventing any releasing movement of the tongue 19. To remove the umbilical clamp, it must be destroyed.

The clamp 10 has an overall length of about 55 mm. The width of each surface 20 is about 6 mm over the major part of its length. The tongue has a length of about 7,5 mm and its width is about 4,3 mm.

The invention is not limited to the precise constructional details hereinbefore described and illustrated in the drawings. The locking members may be applied to any other clamp or locking apparatus whether used for medical purposes or otherwise. The dimensions of the parts may be varied as desired.

The scope of the invention is to be determined solely by the spirit and scope of the appended claims.

I claim:

1. An umbilical cord clamp comprising a one-piece member of polymeric material comprising:

first and second elongated arms extending in a longitudinal direction of the clamp and being provided with facing serrated surfaces and inner and outer ends, connector means connecting said inner ends in a way permitting said arms to pivot relative to one another, a first locking part at the outer end of the first arm, said first locking part comprising a main portion having an inclined front face extending transversely to said longitudinal direction, a pair of parallel side walls on either side of the front face and extending outwardly therefrom in said longitudinal direction, a cross-bar spanning said side walls and being spaced from said front face to form a passageway between said sidewalls and between said crossebar and front face, and a recess in said front face at a location more remote from said second arm than the cross-bar, said recess comprising inclined upper and lower surfaces, said upper surface joining said front face at an acute reentrant angle to fore a nose with said upper surface and a groove with said lower surface, and a second locking part at the outer end of said second arm, said second locking part comprising a tongue dimensioned to fit into said passageway between said side walls and between said front face and said cross-bar, a first hook for receipt in said groove and being located at the end of the tongue and facing said front face of the main portion of said first locking part, said first hook having an acute angled, reentrant, transversely extending opening shaped to receive therein said nose, and a second hook on the tongue and facing said cross-bar, and being so located that it hooks onto said cross-bar when said first hook receives said nose in said opening, the arrangement being such that when the outer ends of said arms are pressed together to close said clamp, said tongue moves into said passageway and said first hook is sprung outward by said inclined front face and then both hooks snap into simultaneous and positive engagement respectively with the nose and cross-bar of said first locking part, the snap providing an audible indication, and the arrangement also providing a visual indication, that the clamp is permanently locked.

2. A clamp as claimed in claim 1 wherein said cross-bar has an inner face opposite to said front face of the main portion of the first locking part and an under surface which is most remote from said second arm, said inner face and under surface meeting at an acute angle to form a pointed corner, and wherein said secondary hook has an acute angled reentrant opening shaped to receive therein said pointed corner.

3. A clamp as claimed in claim 1 in which said cross-bar is located closer to the second arm than is the groove.

* * * * *